(12) United States Patent
Lee et al.

(10) Patent No.: US 6,800,474 B1
(45) Date of Patent: Oct. 5, 2004

(54) TREHALOSE SYNTHASE PROTEIN, GENE, PLASMIDS, MICROORGANISMS, AND A PROCESS FOR PRODUCING TREHALOSE

(75) Inventors: Se Yong Lee, Seoul (KR); Eun Kyung Song, Kyungkee-do (KR); Yearn Hung Park, Seoul (KR); Sang Ho Kwon, Kyungkee-do (KR); Kwang Ho Lee, Seoul (KR); Chang Gyeom Kim, Seoul (KR); Jin Ho Lee, Kyungkee-do (KR); Sung Oh Chung, Kyungkee-do (KR); Yeong Joong Jeon, Seoul (KR)

(73) Assignee: Cheil Jedang Corporation, Seoul (KR)

( * ) Notice: Subject to any disclaimer, the term of this patent is extended or adjusted under 35 U.S.C. 154(b) by 0 days.

(21) Appl. No.: 09/937,215

(22) PCT Filed: Mar. 24, 1999

(86) PCT No.: PCT/KR99/00131

§ 371 (c)(1), (2), (4) Date: Feb. 6, 2002

(87) PCT Pub. No.: WO00/56868

PCT Pub. Date: Sep. 28, 2000

(51) Int. Cl.$^7$ .......................... C12N 9/90; C12N 15/01; C12P 19/12

(52) U.S. Cl. ............... 435/233; 435/100; 435/320.1; 435/252.9; 435/252.33; 536/23.2

(58) Field of Search .............. 435/233, 320.1, 435/252.33, 100, 253.3; 536/23.2

(56) References Cited

U.S. PATENT DOCUMENTS 5,538,883 A * 7/1996 Nishimoto et al. ......... 435/200

FOREIGN PATENT DOCUMENTS

| EP | 0 636 693 A2 | 2/1995 |
| EP | 0 704 531 A2 | 4/1996 |
| JP | 09098779 A | 4/1997 |

OTHER PUBLICATIONS

Nishimoto, T, et al. (1995) Biosci. Biotech. Biochem. 59(11), 2189–2190.*
Ohguchi, M., et al. (1997) J. Ferm. Bioeng. 84(4), 358–360.*

* cited by examiner

Primary Examiner—Charles L. Patterson, Jr.
(74) Attorney, Agent, or Firm—Birch, Stewart, Kolasch & Birch, LLP

(57) ABSTRACT

The present invention relates to a trehalose-producing microorganism and a process for producing trehalose. It also to a novel trehalose synthase protein, a trehalose synthase gene, recombinant plasmids carrying said trehalose synthase gene, and transformed microorganism with said recombinant plasmids.

9 Claims, 6 Drawing Sheets

SEQUENCE LISTING

<160> NUMBER OF SEQ ID NOS: 6

<210> SEQ ID NO 1
<211> LENGTH: 4753
<212> TYPE: DNA
<213> ORGANISM: Pseudomonas stutzeri
<220> FEATURE:
<221> NAME/KEY: CDS
<222> LOCATION: (1537)..(3603)
<223> OTHER INFORMATION:

<400> SEQUENCE: 1

```
gatcgctggc gtactgcagg tagagcaggc gcatcggccc ccagggcgca tcggccggct        60
ccgctgtgcc ctgctggttc atgaagcgga cgaagcggcc atcgcggaac cgtggacgcc       120
attcggggct gtccgggtcg cggctgtcgg tgagcgtgcg ccacaggtcg ctgcgaaacg       180
gcggaccgct ccaaagcgcg ccgtggatgg gatcgccgag cagttcgtgc agctcccagg       240
aacgttgcga atgcagcgcg ccgaggctca ggccatgcag atacaggcgc ggtcggcgtt       300
cggccggcag ttcggtccag tagccataga tctcggcgaa tagcgcgcgg gccacgtcgc       360
ggccgtagtc ggcctccacc agcagcgcca gcgggctgtt cagataggag tactgcaacg       420
ccacgctggc gatatcgccg tggtgcaggt attccactgc gttcatcgcc gccgggtcga       480
tccagccggt accggtgggc gtcaccagca ccagcaccga tcgctcgaag cgccgctgc        540
gctgcagctc gcgcaaggcc agacgcgccc gctggcgcgg gtctctgcc gcgcgcagac        600
cgacgtagac gcgaatcggc tcgagcgccg agcggccgct caagacgctg atatccgccg       660
ccgacgggcc ggagccgatg aactcgcggc cggtgcggcc cagctcctcc cagcgcagca       720
acgaggcccg gctgccgctt ttcagcgcg aggccggtgg cgccgtctcc ggttcgatca        780
gggcgtcgta ctgcgcgaag gatgcgtcca gcatgcgcag tgcccgcgcc gccagcacat       840
cgctgagcag cgaccagaac agcgccagcc caccagcac gccgatcacg ttggccaggc        900
gccgtggcag cacgcggtcg gcgtgccgcg agacgaagcg cgacaccagc cgatacagac       960
gcgccagcgt cagcaggatg agaaaggtcg ccagcgcgt gagaatgact tcgagcaggt       1020
gcgcactgct caccggcggc atgcccatca gcgcgcgtac cgcgttctgc cagccggcga      1080
cctggctgag gaaatacccg gccagcagca ggcagccgac cgcgatcagc agattgaccc      1140
gctcgcgctg ccagcctggg cgctccggca gttccagata gcgccacagc cagcgccaga      1200
acacgccgag gccatagccc accgccagcc gcgcgccggc cagcacgccc tggctcagcg      1260
tcgagcgcgg cagcagcgat ggcgtcagcg ccgcgcagaa gaacagcgtg cccagcagca      1320
ggccgaaacc ggacagcgag cgccagatat agaggacggg caggtgcagc atgaagatct      1380
ccgcggtcgg gtgacggcgt cgcgcctcgg catatcgagg cgtgtccggt cgtgcggttc      1440
ccgtgatggt ccgcagcagg ccaatccgat gcaacgatgg ccgagcggcc gactcaaacg      1500
tctacatttc cctagtgctg ccggaaccga tcgccg atg agc atc cca gac aac         1554
                                         Met Ser Ile Pro Asp Asn
                                         1               5 acc tat atc gaa tgg ctg gtc agc cag tcc atg ctg cat gcg gcc cgc         1602
Thr Tyr Ile Glu Trp Leu Val Ser Gln Ser Met Leu His Ala Ala Arg
         10                  15                  20 gag cgg tcg cgt cat tac gcc ggc cag gcg cgt ctc tgg cag cgg cct         1650
Glu Arg Ser Arg His Tyr Ala Gly Gln Ala Arg Leu Trp Gln Arg Pro
     25                  30                  35 tat gcc cag gcc cgc ccg cgc gat gcc agc gcc atc gcc tcg gtg tgg         1698
Tyr Ala Gln Ala Arg Pro Arg Asp Ala Ser Ala Ile Ala Ser Val Trp
 40                  45                  50 ttc acc gcc tat ccg gcg gcc atc atc acg ccg gaa ggc ggc acg gta         1746
Phe Thr Ala Tyr Pro Ala Ala Ile Ile Thr Pro Glu Gly Gly Thr Val
 55                  60                  65                  70 ctc gag gcc ctc ggc gac gac cgc ctc tgg agt gcg ctc tcc gaa ctc         1794
Leu Glu Ala Leu Gly Asp Asp Arg Leu Trp Ser Ala Leu Ser Glu Leu
             75                  80                  85 ggc gtg cag ggc atc cac aac ggg ccg atg aag cgt tcc ggt ggc ctg         1842
Gly Val Gln Gly Ile His Asn Gly Pro Met Lys Arg Ser Gly Gly Leu
         90                  95                 100
```

-continued

| | | |
|---|---|---|
| cgc gga cgc gag ttc acc ccg acc atc gac ggc aac ttc gac cgc atc<br>Arg Gly Arg Glu Phe Thr Pro Thr Ile Asp Gly Asn Phe Asp Arg Ile<br>            105                     110                    115 | 1890 |
| agc ttc gat atc gac ccg agc ctg ggg acc gag gag cag atg ctg cag<br>Ser Phe Asp Ile Asp Pro Ser Leu Gly Thr Glu Glu Gln Met Leu Gln<br>120                     125                     130 | 1938 |
| ctc agc cgg gtg gcc gcg gcg cac aac gcc atc gtc atc gac gac atc<br>Leu Ser Arg Val Ala Ala Ala His Asn Ala Ile Val Ile Asp Asp Ile<br>135                   140                 145                 150 | 1986 |
| gtg ccg gca cac acc ggc aag ggt gcc gac ttc cgc ctc gcg gaa atg<br>Val Pro Ala His Thr Gly Lys Gly Ala Asp Phe Arg Leu Ala Glu Met<br>                  155                    160               165 | 2034 |
| gcc tat ggc gac tac ccc ggg ctg tac cac atg gtg gaa atc cgc gag<br>Ala Tyr Gly Asp Tyr Pro Gly Leu Tyr His Met Val Glu Ile Arg Glu<br>                  170                    175               180 | 2082 |
| gag gac tgg gag ctg ctg ccc gag gtg ccg gcc ggg cgt gat tcg gtc<br>Glu Asp Trp Glu Leu Leu Pro Glu Val Pro Ala Gly Arg Asp Ser Val<br>                  185                    190               195 | 2130 |
| aac ctg ctg ccg ccg gtg gtc gac cgg ctc aag gaa aag cac tac atc<br>Asn Leu Leu Pro Pro Val Val Asp Arg Leu Lys Glu Lys His Tyr Ile<br>200                     205                     210 | 2178 |
| gtc ggc cag ctg cag cgg gtg atc ttc ttc gag ccg ggc atc aag gac<br>Val Gly Gln Leu Gln Arg Val Ile Phe Phe Glu Pro Gly Ile Lys Asp<br>215                     220                    225               230 | 2226 |
| acc gac tgg agc gtc acc ggc gag gtc acc ggg gtc gac ggc aag gtg<br>Thr Asp Trp Ser Val Thr Gly Glu Val Thr Gly Val Asp Gly Lys Val<br>                  235                    240               245 | 2274 |
| cgt cgc tgg gtc tat ctg cac tac ttc aag gag ggc cag ccg tcg ctg<br>Arg Arg Trp Val Tyr Leu His Tyr Phe Lys Glu Gly Gln Pro Ser Leu<br>                  250                    255               260 | 2322 |
| aac tgg ctc gac ccg acc ttc gcc gcg cag cag ctg atc atc ggc gat<br>Asn Trp Leu Asp Pro Thr Phe Ala Ala Gln Gln Leu Ile Ile Gly Asp<br>                  265                    270               275 | 2370 |
| gcg ctg cac gcc atc gac gtc acc ggc gcc cgg gtg ctg cgc ctg gac<br>Ala Leu His Ala Ile Asp Val Thr Gly Ala Arg Val Leu Arg Leu Asp<br>280                     285                     290 | 2418 |
| gcc aac ggc ttc ctc ggc gtg gaa cgg cgc gcc gag ggc acg gcc tgg<br>Ala Asn Gly Phe Leu Gly Val Glu Arg Arg Ala Glu Gly Thr Ala Trp<br>295                     300                    305               310 | 2466 |
| tcg gag ggc cac ccg ctg tcc gtc acc ggc aac cag ctg ctc gcc ggg<br>Ser Glu Gly His Pro Leu Ser Val Thr Gly Asn Gln Leu Leu Ala Gly<br>                  315                    320               325 | 2514 |
| gcg atc cgc aag gcc ggc ggc ttc agc ttc cag gag ctg aac ctg acc<br>Ala Ile Arg Lys Ala Gly Gly Phe Ser Phe Gln Glu Leu Asn Leu Thr<br>                  330                    335               340 | 2562 |
| atc gat gac atc gcc gcc atg tcc cac ggc ggg gcc gat ctg tcc tac<br>Ile Asp Asp Ile Ala Ala Met Ser His Gly Gly Ala Asp Leu Ser Tyr<br>345                     350                    355 | 2610 |
| gac ttc atc acc cgc ccg gcc tat cac cat gcg ttg ctc acc ggc gat<br>Asp Phe Ile Thr Arg Pro Ala Tyr His His Ala Leu Leu Thr Gly Asp<br>                  360                    365               370 | 2658 |
| acc gaa ttc ctg cgc atg atg ctg cgc gaa gtg cac gcc ttc ggc atc<br>Thr Glu Phe Leu Arg Met Met Leu Arg Glu Val His Ala Phe Gly Ile<br>375                     380                    385               390 | 2706 |
| gac ccg gcg tca ctg atc cat gcg ctg cag aac cat gac gag ttc acc<br>Asp Pro Ala Ser Leu Ile His Ala Leu Gln Asn His Asp Glu Phe Thr<br>                  395                    400               405 | 2754 |

```
ctg gag ctg gtg cac ttc tgg acg ctg cac gcc tac gac cat tac cac         2802
Leu Glu Leu Val His Phe Trp Thr Leu His Ala Tyr Asp His Tyr His
            410                 415                 420 tac aag ggc cag acc ctg ccc ggc ggc cac ctg cgc gaa cat atc cgc         2850
Tyr Lys Gly Gln Thr Leu Pro Gly Gly His Leu Arg Glu His Ile Arg
        425                 430                 435 gag gaa atg tac gag cgg ctg acc ggc gaa cac gcg ccg tac aac ctc         2898
Glu Glu Met Tyr Glu Arg Leu Thr Gly Glu His Ala Pro Tyr Asn Leu
    440                 445                 450 aag ttc gtc acc aac ggg gtg tcc tgc acc acc gcc agc gtg atc gcc         2946
Lys Phe Val Thr Asn Gly Val Ser Cys Thr Thr Ala Ser Val Ile Ala
455                 460                 465                 470 gcg gcg ctt aac atc cgt gat ctg gac gcc atc ggc ccg gcc gag gtg         2994
Ala Ala Leu Asn Ile Arg Asp Leu Asp Ala Ile Gly Pro Ala Glu Val
                475                 480                 485 gag cag atc cag cgt ctg cat atc ctg ctg gtg atg ttc aat gcc atg         3042
Glu Gln Ile Gln Arg Leu His Ile Leu Leu Val Met Phe Asn Ala Met
            490                 495                 500 cag ccc ggc gtg ttc gcc ctc tcc ggc tgg gat ctg gtc ggc gcc ctg         3090
Gln Pro Gly Val Phe Ala Leu Ser Gly Trp Asp Leu Val Gly Ala Leu
        505                 510                 515 ccg ctg gcg ccc gag cag gtc gag cac ctg atg ggc gat ggc gat acc         3138
Pro Leu Ala Pro Glu Gln Val Glu His Leu Met Gly Asp Gly Asp Thr
    520                 525                 530 cgc tgg atc aat cgc ggc ggc tat gac ctc gcc gat ctg gcg ccg gag         3186
Arg Trp Ile Asn Arg Gly Gly Tyr Asp Leu Ala Asp Leu Ala Pro Glu
535                 540                 545                 550 gcg tcg gtc tcc gcc gaa ggc ctg ccc aag gcc cgc tcg ctg tac ggc         3234
Ala Ser Val Ser Ala Glu Gly Leu Pro Lys Ala Arg Ser Leu Tyr Gly
                555                 560                 565 agc ctg gcc gag cag ctg cag cgg cca ggc tcc ttc gcc tgc cag ctc         3282
Ser Leu Ala Glu Gln Leu Gln Arg Pro Gly Ser Phe Ala Cys Gln Leu
            570                 575                 580 aag cgc atc ctc agc gtg cgc cag gcc tac gac atc gct gcc agc aag         3330
Lys Arg Ile Leu Ser Val Arg Gln Ala Tyr Asp Ile Ala Ala Ser Lys
        585                 590                 595 cag atc ctg att ccg gat gtg cag gcg ccg gga ctc ctg gtg atg gtc         3378
Gln Ile Leu Ile Pro Asp Val Gln Ala Pro Gly Leu Leu Val Met Val
    600                 605                 610 cac gag ctg cct gcc ggc aag ggc gtg cag ctc acg gca ctg aac ttc         3426
His Glu Leu Pro Ala Gly Lys Gly Val Gln Leu Thr Ala Leu Asn Phe
615                 620                 625                 630 agc gcc gag ccg gtc agc gag acc atc tgc ctg ccc ggc gtg gcg ccc         3474
Ser Ala Glu Pro Val Ser Glu Thr Ile Cys Leu Pro Gly Val Ala Pro
                635                 640                 645 ggc ccg gtg gtg gac atc att cac gag agt gtg gag ggc gac ctc acc         3522
Gly Pro Val Val Asp Ile Ile His Glu Ser Val Glu Gly Asp Leu Thr
            650                 655                 660 gac aac tgc gag ctg cag atc aac ctc gac ccg tac gag ggg ctt gcc         3570
Asp Asn Cys Glu Leu Gln Ile Asn Leu Asp Pro Tyr Glu Gly Leu Ala
        665                 670                 675 ctg cgt gtg gtg agc gcc gcg ccg ccg gtg atc tgagcgccct cttcgcgcgc      3623
Leu Arg Val Val Ser Ala Ala Pro Pro Val Ile
    680                 685 cccgggtccg ccgctatagt gcgcagcgcc tggggcgcgc attgccctcg ccgtcgagac      3683
cagcccgtgt cgttcacttc gcttttccgc cttgcgctgc tgccgctggc gctgcttgcc      3743
gcacccgtct gggcgcagac cgcctgcccg cccggccagc agccgatctg cctgagcggc      3803
agctgcctct gcgtgccggc cgccgccagc gatccacagg cggtctacga ccgcgtccag      3863
```

-continued

```
cgtatggcta cgctggccct gcagaactgg atccagcagt cgcgcgaccg cctgatggcc    3923
ggcggcgtcg agccgatacc gctgcacatc cgctcgcagc tcgagccgta tttcgatctt    3983
gccgtgctgg agagtgcgcg gtaccgcgtc ggcgacgagg tggtgctgac tgccggcaac    4043
accctgctgc gcaacccgga cgtcaatgcc gtgaccctga tcgacgtcat cgtcttccgc    4103
cacgaggagg atgcccggga caacgtcgcg ctctgggccc atgagctcaa gcacgtcgag    4163
caatatctgg actggggcgt cgccgagttc gcccggcgct atacgcagga tttccgtgcc    4223
gtggagcgcc cggcctatgc gctggagcgt gaggtggaag aggccctgcg cgagacgcag    4283
acgcggcgct gagcgagctg atcggtgctg ctgcccgcac tgggctgaag cccaccaatg    4343
acgccggcga aaacgaaaaa ccccgccgag gcggggtttc tgacgcgggt tgtgcggtca    4403
gctcagaacg ccgggaccac ggcgcccttg tactttttcct cgatgaactg gcgtacttgc    4463
tcgctgtgca gcgcggcagc cagtttctgc atggcatcgc tgtccttgtt gtccggacgg    4523
gcgaccagaa tgttcacgta tggcgagtcg ctgccctcga tcaccagggc gtcctgggtc    4583
gggttcagct tggcttccag cgcgtagttg gtgttgatca gcgccaggtc gacctgggtc    4643
agcacgcgcg gcagagtcgc ggcttccagt tcgcggatct tgatcttctt cgggttctcg    4703
gcgatgtctt cggcgtggcg gtgatgccgg cgccgtcctt cagaccgatc                4753
```

<210> SEQ ID NO 2
<211> LENGTH: 689
<212> TYPE: PRT
<213> ORGANISM: Pseudomonas stutzeri

<400> SEQUENCE: 2

```
Met Ser Ile Pro Asp Asn Thr Tyr Ile Glu Trp Leu Val Ser Gln Ser
1               5                   10                  15

Met Leu His Ala Ala Arg Glu Arg Ser Arg His Tyr Ala Gly Gln Ala
            20                  25                  30

Arg Leu Trp Gln Arg Pro Tyr Ala Gln Ala Arg Pro Arg Asp Ala Ser
        35                  40                  45

Ala Ile Ala Ser Val Trp Phe Thr Ala Tyr Pro Ala Ala Ile Ile Thr
    50                  55                  60

Pro Glu Gly Gly Thr Val Leu Glu Ala Leu Gly Asp Asp Arg Leu Trp
65                  70                  75                  80

Ser Ala Leu Ser Glu Leu Gly Val Gln Gly Ile His Asn Gly Pro Met
                85                  90                  95

Lys Arg Ser Gly Gly Leu Arg Gly Arg Glu Phe Thr Pro Thr Ile Asp
            100                 105                 110

Gly Asn Phe Asp Arg Ile Ser Phe Asp Ile Asp Pro Ser Leu Gly Thr
        115                 120                 125

Glu Glu Gln Met Leu Gln Leu Ser Arg Val Ala Ala His Asn Ala
    130                 135                 140

Ile Val Ile Asp Asp Ile Val Pro Ala His Thr Gly Lys Gly Ala Asp
145                 150                 155                 160

Phe Arg Leu Ala Glu Met Ala Tyr Gly Asp Tyr Pro Gly Leu Tyr His
                165                 170                 175

Met Val Glu Ile Arg Glu Glu Asp Trp Glu Leu Leu Pro Glu Val Pro
            180                 185                 190

Ala Gly Arg Asp Ser Val Asn Leu Leu Pro Pro Val Val Asp Arg Leu
        195                 200                 205
```

-continued

```
Lys Glu Lys His Tyr Ile Val Gly Gln Leu Gln Arg Val Ile Phe Phe
    210                 215                 220
Glu Pro Gly Ile Lys Asp Thr Asp Trp Ser Val Thr Gly Glu Val Thr
225                 230                 235                 240
Gly Val Asp Gly Lys Val Arg Arg Trp Val Tyr Leu His Tyr Phe Lys
                245                 250                 255
Glu Gly Gln Pro Ser Leu Asn Trp Leu Asp Pro Thr Phe Ala Ala Gln
                260                 265                 270
Gln Leu Ile Ile Gly Asp Ala Leu His Ala Ile Asp Val Thr Gly Ala
            275                 280                 285
Arg Val Leu Arg Leu Asp Ala Asn Gly Phe Leu Gly Val Glu Arg Arg
    290                 295                 300
Ala Glu Gly Thr Ala Trp Ser Glu Gly His Pro Leu Ser Val Thr Gly
305                 310                 315                 320
Asn Gln Leu Leu Ala Gly Ala Ile Arg Lys Ala Gly Phe Ser Phe
                325                 330                 335
Gln Glu Leu Asn Leu Thr Ile Asp Asp Ile Ala Ala Met Ser His Gly
            340                 345                 350
Gly Ala Asp Leu Ser Tyr Asp Phe Ile Thr Arg Pro Ala Tyr His His
    355                 360                 365
Ala Leu Leu Thr Gly Asp Thr Glu Phe Leu Arg Met Met Leu Arg Glu
370                 375                 380
Val His Ala Phe Gly Ile Asp Pro Ala Ser Leu Ile His Ala Leu Gln
385                 390                 395                 400
Asn His Asp Glu Phe Thr Leu Glu Leu Val His Phe Trp Thr Leu His
                405                 410                 415
Ala Tyr Asp His Tyr His Tyr Lys Gly Gln Thr Leu Pro Gly Gly His
            420                 425                 430
Leu Arg Glu His Ile Arg Glu Glu Met Tyr Glu Arg Leu Thr Gly Glu
    435                 440                 445
His Ala Pro Tyr Asn Leu Lys Phe Val Thr Asn Gly Val Ser Cys Thr
450                 455                 460
Thr Ala Ser Val Ile Ala Ala Leu Asn Ile Arg Asp Leu Asp Ala
465                 470                 475                 480
Ile Gly Pro Ala Glu Val Glu Gln Ile Gln Arg Leu His Ile Leu Leu
                485                 490                 495
Val Met Phe Asn Ala Met Gln Pro Gly Val Phe Ala Leu Ser Gly Trp
            500                 505                 510
Asp Leu Val Gly Ala Leu Pro Leu Ala Pro Glu Gln Val Glu His Leu
    515                 520                 525
Met Gly Asp Gly Asp Thr Arg Trp Ile Asn Arg Gly Gly Tyr Asp Leu
530                 535                 540
Ala Asp Leu Ala Pro Glu Ala Ser Val Ser Ala Glu Gly Leu Pro Lys
545                 550                 555                 560
Ala Arg Ser Leu Tyr Gly Ser Leu Ala Glu Gln Leu Gln Arg Pro Gly
                565                 570                 575
Ser Phe Ala Cys Gln Leu Lys Arg Ile Leu Ser Val Arg Gln Ala Tyr
            580                 585                 590
Asp Ile Ala Ala Ser Lys Gln Ile Leu Ile Pro Asp Val Gln Ala Pro
    595                 600                 605
Gly Leu Leu Val Met Val His Glu Leu Pro Ala Gly Lys Gly Val Gln
610                 615                 620
```

-continued

```
Leu Thr Ala Leu Asn Phe Ser Ala Glu Pro Val Ser Glu Thr Ile Cys
625                 630                 635                 640

Leu Pro Gly Val Ala Pro Gly Pro Val Val Asp Ile Ile His Glu Ser
                645                 650                 655

Val Glu Gly Asp Leu Thr Asp Asn Cys Glu Leu Gln Ile Asn Leu Asp
            660                 665                 670

Pro Tyr Glu Gly Leu Ala Leu Arg Val Val Ser Ala Ala Pro Pro Val
        675                 680                 685

Ile
```

<210> SEQ ID NO 3
<211> LENGTH: 13
<212> TYPE: PRT
<213> ORGANISM: Thermus aquaticus

<400> SEQUENCE: 3

```
Met Asp Pro Leu Trp Tyr Lys Asp Ala Val Ile Tyr Gln
1               5                   10
```

<210> SEQ ID NO 4
<211> LENGTH: 18
<212> TYPE: PRT
<213> ORGANISM: Pimelobacter sp.

<400> SEQUENCE: 4

```
Ser Thr Val Leu Gly Glu Glu Pro Glu Trp Phe Arg Thr Ala Val Phe
1               5                   10                  15

Tyr Glu
```

<210> SEQ ID NO 5
<211> LENGTH: 11
<212> TYPE: PRT
<213> ORGANISM: Pseudomonas putida

<400> SEQUENCE: 5

```
Gly Lys Trp Pro Arg Pro Ala Ala Phe Ile Asp
1               5                   10
```

<210> SEQ ID NO 6
<211> LENGTH: 12
<212> TYPE: PRT
<213> ORGANISM: Escherichia coli

<400> SEQUENCE: 6

```
Ser Ile Pro Asp Asn Thr Tyr Ile Glu Trp Leu Val
1               5                   10
```

TREHALOSE SYNTHASE PROTEIN, GENE, PLASMIDS, MICROORGANISMS, AND A PROCESS FOR PRODUCING TREHALOSE

This application is the national phase under 35 U.S.C. § 371 of PCT International Application No. PCT/KR99/00131 which has an International filing date of Mar. 24, 1999, which designated the United States of America and was published in English.

BACKGROUND OF THE INVENTION

1. Field of the Invention

The present invention relates to a trehalose-producing microorganism and a process for producing trehalose. It also relates to a novel trehalose synthase protein, a trehalose synthase gene, recombinant plasmids carrying said trehalose synthase gene, and transformed microorganisms with said recombinant plasmids.

2. Description of the Prior Art

Trehalose is a non-reducing disaccharide, two saccharides of which are linked by α-1,1 bond: α-D-glucopyranosyl-α-D-glucopyranoside. It has wide application in medicines, foods, and cosmetics. However, its utilization has been greatly restricted because its production to date has been inefficient and expensive.

Japanese Laid-open Patent Nos. Hei5-91890 and Hei6-145186 disclose methods for extracting trehalose from yeasts. There are several methods for isolating trehalose from fermented microorganism cultures, such as Arthrobacter (T. Suzuki, Agric. Biol. Chem., 33(2), 1969), Nocardia (Japanese Laid-open Patent No. Sho 50–154485), Micrococcus (Japanese Laid-open Patent No. Hei6-319578), amino acid-fermenting yeast, Brevibacterium (Japanese Laid-open Patent No. Hei5-211882), and yeast (Yoshikwa, etc., Biosci. Biotech. Biochem., 1994, 58, 1226–12300). Additionally, a method for producing trehalose by using recombinant plants including bacterial genes capable of converting glucose into trehalose is described in M. Scher, Food Processing, April, 95–96, 1993. Japanese Laid-open Patent No. 83-216695 discloses a method for converting maltose into trehalose by using maltose phosphorylase and trehalose phosphorylase. However, these methods are not effective, because their procedures are complicated and their yields are low.

Several enzymatic methods have been published recently. Japanese Laid-open Patent No. Hei7-143876 and EPO 628630 A2 discloses a two-step enzymatic conversion method in which starch is converted into trehalose by maltooligosyl trehalose synthase and maltooligosyl trehalose trehalohydrolase. Japanses Laid-open Patent No. Hei7-170977 and Korean Laid-open Patent No.95-3444 disclose one-step enzymatic conversion methods in which maltose is directly converted into trehalose by trehalose synthase. However, there is still a need to increase the titer of the trehalose synthase enzyme so that production of trehalose from maltose becomes more efficient in yield and cost.

We have invested much effort over the last several years in isolating microorganisms able to convert maltose into trehalose from soil. We have successfully screened a novel strain which highly expresses trehalose and, unexpectedly, generates no byproducts, unlike all known microorganisms. Its morphological and physiological characteristics identify it as a novel *Pseudomonas stutzeri* strain. This strain has been designated as *Pseudomonas stutzeri* CJ38.

We isolated a trehalose synthase gene from chromosomes of *Pseudomonas stutzeri* CJ38 and determined its nucleotide sequence by cloning it into known vector pUC 18 with restriction enzyme Sau3AI. In addition, we isolated a trehalose synthase protein from *Pseudomonas stutzeri* CJ38 and determined its amino acid sequence using standard methods. It was found that these sequences are apparently different from the sequences of the trehalose synthase gene and all proteins known hitherto. This invention was achieved by constructing recombinant plasmnids carrying the trehalose synthase gene so that the trehalose synthase enzyme encoded in said gene can be expressed in large amounts.

SUMMARY OF THE INVENTION

The present invention provides a novel microorganism, *Pseudomonas stutzeri* CJ38, that produces trehalose from maltose. This strain was deposited at the Korea Culture Center of Microorganisms, Seoul, Korea, as the accession number KCCM 10150 on Feb. 12, 1999 under the Budapest Treaty. This strain is very valuable as it does not generate byproducts such as glucose when converts maltose into trehalose.

The present invention also provides SEQ ID NO: 2, which is a novel trehalose synthase protein with the following amino acid sequence:

| Met | Ser | Ile | Pro | Asp | Asn | Thr | Tyr | Ile | Glu | Trp | Leu | Val | Ser | Gln |
|---|---|---|---|---|---|---|---|---|---|---|---|---|---|---|
| | | | | 5 | | | | | 10 | | | | | 15 |
| Ser | Met | Leu | His | Ala | Ala | Arg | Glu | Arg | Ser | Arg | His | Tyr | Ala | Gly |
| | | | | 20 | | | | | 25 | | | | | 30 |
| Gln | Ala | Arg | Leu | Trp | Gln | Arg | Pro | Try | Ala | Gln | Ala | Arg | Pro | Arg |
| | | | | 35 | | | | | 40 | | | | | 45 |
| Asp | Ala | Ser | Ala | Ile | Ala | Ser | Val | Trp | Phe | Thr | Ala | Tyr | Pro | Ala |
| | | | | 50 | | | | | 55 | | | | | 60 |
| Ala | Ile | Ile | Thr | Pro | Glu | Gly | Gly | Thr | Val | Leu | Glu | Ala | Leu | Gly |
| | | | | 65 | | | | | 70 | | | | | 75 |

-continued

```
Asp Asp Arg Leu Trp Ser Ala Leu Ser Glu Leu Gly Val Gln Gly
                80                  85                  90

Ile His Asn Gly Pro Met Lys Arg Ser Gly Gly Leu Arg Gly Arg
                95                 100                 105

Glu Phe Thr Pro Thr Ile Asp Gly Asn Phe Asp Arg Ile Ser Phe
               110                 115                 120

Asp Ile Asp Pro Ser Leu Gly Thr Glu Glu Gln Met Leu Gln Leu
               125                 130                 135

Ser Arg Val Ala Ala Ala His Asn Ala Ile Val Ile Asp Asp Ile
               140                 145                 150

Val Pro Ala His Thr Gly Lys Gly Ala Asp Phe Arg Leu Ala Glu
               155                 160                 165

Met Ala Tyr Gly Asp Tyr Pro Gly Leu Tyr His Met Val Glu Ile
               170                 175                 180

Arg Glu Glu Asp Trp Glu Leu Leu Pro Glu Val Pro Ala Gly Arg
               185                 190                 195

Asp Ser Val Asn Leu Leu Pro Pro Val Val Asp Arg Leu Lys Glu
               200                 205                 210

Lys His Tyr Ile Val Gly Gln Leu Gln Arg Val Ile Phe Phe Glu
               215                 220                 225

Pro Gly Ile Lys Asp Thr Asp Trp Ser Val Thr Gly Glu Val Thr
               230                 235                 240

Gly Val Asp Gly Lys Val Arg Arg Trp Val Tyr Leu His Tyr Phe
               245                 250                 255

Lys Glu Gly Gln Pro Ser Lue Asn Trp Leu Asp Pro Thr Phe Ala
               260                 265                 270

Ala Gln Gln Leu Ile Ile Gly Asp Ala Leu His Ala Ile Asp Val
               275                 280                 285

Thr Gly Ala Arg Val Leu Arg Leu Asp Ala Asn Gly Phe Leu Gly
               290                 295                 300

Val Glu Arg Arg Ala Glu Gly Thr Ala Trp Ser Glu Gly His Pro
               305                 310                 315

Leu Ser Val Thr Gly Asn Gln Leu Leu Ala Gly Ala Ile Arg Lys
               320                 325                 330

Ala Gly Gly Phe Ser Phe Gln Glu Leu Asn Leu Thr Ile Asp Asp
               335                 340                 345

Ile Ala Ala Met Ser His Gly Gly Ala Asp Leu Ser Tyr Asp Phe
               350                 355                 360

Ile Thr Arg Pro Ala Tyr His His Ala Leu Leu Thr Gly Asp Thr
               365                 370                 375
```

-continued

| | | | | | | | | | | | |
|---|---|---|---|---|---|---|---|---|---|---|---|
|Glu|Phe|Leu|Arg|Met|Met|Leu|Arg|Glu|Val|His|Ala|Phe|Gly|Ile|
| | | |380| | | |385| | | |390|
|Asp|Pro|Ala|Ser|Leu|Ile|His|Ala|Leu|Gln|Asn|His|Asp|Glu|Leu|
| | | |395| | | |400| | | |405|
|Thr|Leu|Glu|Leu|Val|His|Phe|Trp|Thr|Leu|His|Ala|Tyr|Asp|His|
| | | |410| | | |415| | | |420|
|Tyr|His|Tyr|Lys|Gly|Gln|Thr|Leu|Pro|Gly|Gly|His|Leu|Arg|Glu|
| | | |425| | | |430| | | |435|
|His|Ile|Arg|Glu|Glu|Met|Tyr|Glu|Arg|Leu|Thr|Gly|Glu|His|Ala|
| | | |440| | | |445| | | |450|
|Pro|Tyr|Asn|Leu|Lys|Phe|Val|Thr|Asn|Gly|Val|Ser|Cys|Thr|Thr|
| | | |455| | | |460| | | |465|
|Ala|Ser|Val|Ile|Ala|Ala|Ala|Leu|Asn|Ile|Arg|Asp|Leu|Asp|Ala|
| | | |470| | | |475| | | |480|
|Ile|Gly|Pro|Ala|Glu|Val|Glu|Gln|Ile|Gln|Arg|Leu|His|Ile|Leu|
| | | |485| | | |490| | | |495|
|Leu|Val|Met|Phe|Asn|Ala|Met|Gln|Pro|Gly|Val|Phe|Ala|Leu|Ser|
| | | |500| | | |505| | | |510|
|Gly|Trp|Asp|Leu|Val|Gly|Ala|Leu|Pro|Leu|Ala|Pro|Glu|Gln|Val|
| | | |515| | | |520| | | |525|
|Glu|His|Leu|Met|Gly|Asp|Gly|Asp|Thr|Arg|Trp|Ile|Asn|Arg|Gly|
| | | |530| | | |535| | | |540|
|Gly|Tyr|Asp|Leu|Ala|Asp|Leu|Ala|Pro|Glu|Ala|Ser|Val|Ser|Ala|
| | | |545| | | |550| | | |555|
|Glu|Gly|Leu|Pro|Lys|Ala|Arg|Ser|Leu|Tyr|Gly|Ser|Leu|Ala|Glu|
| | | |560| | | |565| | | |570|
|Gln|Leu|Gln|Arg|Pro|Gly|Ser|Phe|Ala|Cys|Gln|Leu|Lys|Arg|Ile|
| | | |575| | | |580| | | |585|
|Leu|Ser|Val|Arg|Gln|Ala|Tyr|Asp|Ile|Ala|Ala|Ser|Lys|Gln|Ile|
| | | |590| | | |595| | | |600|
|Leu|Ile|Pro|Asp|Val|Gln|Ala|Pro|Gly|Leu|Leu|Val|Met|Val|His|
| | | |605| | | |610| | | |615|
|Glu|Leu|Pro|Ala|Gly|Lys|Gly|Val|Gln|Leu|Thr|Ala|Leu|Asn|Phe|
| | | |620| | | |625| | | |630|
|Ser|Ala|Glu|Pro|Val|Ser|Glu|Thr|Ile|Cys|Leu|Pro|Gly|Val|Ala|
| | | |635| | | |640| | | |645|
|Pro|Gly|Pro|Val|Val|Asp|Ile|Ile|His|Glu|Ser|Val|Glu|Gly|Asp|
| | | |650| | | |655| | | |660|

```
                         -continued
Leu Thr Asp Asn Cys Glu Leu Gln Ile Asn Leu Asp Pro Tyr Glu
                665                 670                 675

Gly Leu Ala Leu Arg Val Val Ser Ala Ala Pro Pro Val Ile.
                680                 685
```

In addition, the present invention provides SEQ ID NO: 1, which is a novel trehalose synthase gene with the following nucleotide sequence:

```
GATCGCTGGC GTACTGCAGG TAGAGCAGGC GCATCGGCCC CCAGGGCGCA TCGGCCGGCT      60

CCGCTGTGCC CTGCTGGTTC ATGAAGCGGA CGAAGCGGCC ATCGCGGAAC CGTGGACGCC     120

ATTCGGGGCT GTCCGGGTCG CGGCTGTCGG TGAGCGTGCG CCACAGGTCG CTGCGAAACG     180

GCGGACCGCT CCAAAGCGCG CCGTGGATGG GATCGCCGAG CAGTTCGTGC AGCTCCCAGG     240

AACGTTGCGA ATGCAGCGCG CCGAGGCTCA GGCCATGCAG ATACAGGCGC GGTCGGCGTT     300

CGGCCGGCAG TTCGGTCCAG TAGCCATAGA TCTCGGCGAA TAGCGCGCGG GCCACGTCGC     360

GGCCGTAGTC GGCCTCCACC AGCAGCGCCA GCGGGCTGTT CAGATAGGAG TACTGCAACG     420

CCACGCTGGC GATATCGCCG TGGTGCAGGT ATTCCACTGC GTTCATCGCC GCCGGGTCGA     480

TCCAGCCGGT ACCGGTGGGC GTCACCAGCA CCAGCACCGA TCGCTCGAAG GCGCCGCTGC     540

GCTGCAGCTC GCGCAAGGCC AGACGCGCCC GCTGGCGCGG GGTCTCTGCC GCGCGCAGAC     600

CGACGTAGAC GCGAATCGGC TCGAGCGCCG AGCGGCCGCT CAAGACGCTG ATATCCGCCG     660

CCGACGGGCC GGAGCCGATG AACTCGCGGC CGGTGCGGCC CAGCTCCTCC CAGCGCAGCA     720

ACGAGGCCCG GCTGCCGCTT TTCAGCGGCG AGGCCGGTGG CGCCGTCTCC GGTTCGATCA     780

GGGCGTCGTA CTGCGCGAAG GATGCGTCCA GCATGCGCAG TGCCCGCGCC GCCAGCACAT     840

CGCTGAGCAG CGACCAGAAC AGCGCCAGCG CCACCAGCAC GCCGATCACG TTGGCCAGGC     900

GCCGTGGCAG CACGCGGTCG GCGTGCCGCG AGACGAAGCG CGACACCAGC CGATACAGAC     960

GCGCCAGCGT CAGCAGGATG AGAAAGGTCG CCAGCGCGGT GAGAATGACT TCGAGCAGGT    1020

GCGCACTGCT CACCGGCGGC ATGCCCATCA GCGCGCGTAC CGCGTTCTGC CAGCCGGCGA    1080

CCTGGCTGAG GAAATACCCG GCCAGCAGCA GGCAGCCGAC CGCGATCAGC AGATTGACCC    1140

GCTCGCGCTG CCAGCCTGGG CGCTCCGGCA GTTCCAGATA GCGCCACAGC CAGCGCCAGA    1200

ACACGCCGAG GCCATAGCCC ACCGCCAGCG CCGCGCCGGC CAGCACGCCC TGGCTCAGCG    1260

TCGAGCGCGG CAGCAGCGAT GGCGTCAGCG CCGCGCAGAA GAACAGCGTG CCCAGCAGCA    1320

GGCCGAAACC GGACAGCGAG CGCCAGATAT AGAGGACGGG CAGGTGCAGC ATGAAGATCT    1380

CCGCGGTCGG GTGACGGCGT CGCGCCTCGG CATATCGAGG CGTGTCCGGT CGTGCGGTTC    1440

CCGTGATGGT CCGCAGCAGG CCAATCCGAT GCAACGATGG CCGAGCGGCC GACTCAAACG    1500

TCTACATTTC CCTAGTGCTG CCGGAACCGA TCGCCG                              1536

ATG AGC ATC CCA GAC AAC ACC TAT ATC GAA TGG CTG GTC AGC CAG TCC     1584
Met Ser Ile Pro Asp Asn Thr Tyr Ile Glu Trp Leu Val Ser Gln Ser

ATG CTG CAT GCG GCC CGC GAG CGG TCG CGT CAT TAC GCC GGC CAG GCG     1632
Met Leu His Ala Ala Arg Glu Arg Ser Arg His Tyr Ala Gly Gln Ala

CGT CTC TGG CAG CGG CCT TAT GCC CAG GCC CGC CCG CGC GAT GCC AGC     1680
Arg Leu Trp Gln Arg Pro Try Ala Gln Ala Arg Pro Arg Asp Ala Ser

GCC ATC GCC TCG GTG TGG TTC ACC GCC TAT CCG GCG GCC ATC ATC ACG     1728
Ala Ile Ala Ser Val Trp Phe Thr Ala Tyr Pro Ala Ala Ile Ile Thr
```

-continued

```
CCG GAA GGC GGC ACG GTA CTC GAG GCC CTC GGC GAC GAC CGC CTC TGG      1776
Pro Glu Gly Gly Thr Val Leu Glu Ala Leu Gly Asp Asp Arp Leu Trp

AGT GCG CTC TCC GAA CTC GGC GTG CAG GGC ATC CAC AAC GGG CCG ATG      1824
Ser Ala Leu Ser Glu Leu Gly Val Gln Gly Ile His Asn Gly Pro Met

AAG CGT TCC GGT GGC CTG CGC GGA CGC GAG TTC ACC CCG ACC ATC GAC      1872
Lys Arg Ser Gly Gly Leu Arg Gly Arg Glu Phe Thr Pro Thr Ile Asp

GGC AAC TTC GAC CGC ATC AGC TTC GAT ATC GAC CCG AGC CTG GGG ACC      1920
Gly Asn Phe Asp Arg Ile Ser Phe Asp Ile Asp Pro Ser Leu Gly Thr

GAG GAG CAG ATG CTG CAG CTC AGC CGG GTG GCC GCG GCG CAC AAC GCC      1968
Glu Glu Gln Met Leu Gln Leu Ser Arg Val Ala Ala Ala His Asn Ala

ATC GTC ATC GAC GAC ATC GTG CCG GCA CAC ACC GGC AAG GGT GCC GAC      2016
Ile Val Ile Asp Asp Ile Val Pro Ala His Thr Gly Lys Gly Ala Asp

TTC CGC CTC GCG GAA ATG GCC TAT GGC GAC TAC CCC GGG CTG TAC CAC      2064
Phe Arg Leu Ala Glu Met Ala Tyr Gly Asp Tyr Pro Gly Leu Tyr His

ATG GTG GAA ATC CGC GAG GAG GAC TGG GAG CTG CTG CCC GAG GTG CCG      2112
Met Val Glu Ile Arg Glu Glu Asp Trp Glu Leu Leu Pro Glu Val Pro

GCC GGG CGT GAT TCG GTC AAC CTG CTG CCG CCG GTG GTC GAC CGG CTC      2160
Ala Gly Arg Asp Ser Val Asn Leu Leu Pro Pro Val Val Asp Arg Leu

AAG GAA AAG CAC TAC ATC GTC GGC CAG CTG CAG CGG GTG ATC TTC TTC      2208
Lys Glu Lys His Tyr Ile Val Gly Gln Leu Gln Arg Val Ile Phe Phe

GAG CCG GGC ATC AAG GAC ACC GAC TGG AGC GTC ACC GGC GAG GTC ACC      2256
Glu Pro Gly Ile Lys Asp Thr Asp Trp Ser Val Thr Gly Glu Val Thr

GGG GTC GAC GGC AAG GTG CGT CGC TGG GTC TAT CTG CAC TAC TTC AAG      2304
Gly Val Asp Gly Lys Val Arg Arg Trp Val Tyr Leu His Tyr Phe Lys

GAG GGC CAG CCG TCG CTG AAC TGG CTC GAC CCG ACC TTC GCC GCG CAG      2352
Glu Gly Gln Pro Ser Leu Asn Trp Leu Asp Pro Thr Phe Ala Ala Gln

CAG CTG ATC ATC GGC GAT GCG CTG CAC GCC ATC GAC GTC ACC GGC GCC      2400
Gln Leu Ile Ile Gly Asp Ala Leu His Ala Ile Asp Val Thr Gly Ala

CGG GTG CTG CGC CTG GAC GCC AAC GGC TTC CTC GGC GTG GAA CGG CGC      2448
Arg Val Leu Arg Leu Asp Ala Asn Gly Phe Leu Gly Val Glu Arg Arg

GCC GAG GGC ACG GCC TGG TCG GAG GGC CAC CCG CTG TCC GTC ACC GGC      2496
Ala Glu Gly Thr Ala Trp Ser Glu Gly His Pro Leu Ser Val Thr Gly

AAC CAG CTG CTC GCC GGG GCG ATC CGC AAG GCC GGC GGC TTC AGC TTC      2544
Asn Gln Leu Leu Ala Gly Ala Ile Arg Lys Ala Gly Gly Phe Ser Phe

CAG GAG CTG AAC CTG ACC ATC GAT GAC ATC GCC GCC ATG TCC CAC GGC      2592
Gln Glu Leu Asn Leu Thr Ile Asp Asp Ile Ala Ala Met Ser His Gly

GGG GCC GAT CTG TCC TAC GAC TTC ATC ACC CGC CCG GCC TAT CAC CAT      2640
Gly Ala Asp Leu Ser Tyr Asp Phe Ile Thr Arg Pro Ala Tyr His His

GCG TTG CTC ACC GGC GAT ACC GAA TTC CTG CGC ATG ATG CTG CGC GAA      2688
Ala Leu Leu Thr Gly Asp Thr Glu Phe Leu Arg Met Met Leu Arg Glu

GTG CAC GCC TTC GGC ATC GAC CCG GCG TCA CTG ATC CAT GCG CTG CAG      2736
Val His Ala Phe Gly Ile Asp Pro Ala Ser Leu Ile His Ala Leu Gln

AAC CAT GAC GAG TTC ACC CTG GAG CTG GTG CAC TTC TGG ACG CTG CAC      2784
Asn His Asp Glu Phe Thr Leu Glu Leu Val His Phe Trp Thr Leu His

GCC TAC GAC CAT TAC CAC TAC AAG GGC CAG ACC CTG CCC GGC GGC CAC      2832
Ala Tyr Asp His Tyr His Tyr Lys Gly Gln Thr Leu Pro Gly Gly His

CTG CGC GAA CAT ATC CGC GAG GAA ATG TAC GAG CGG CTG ACC GGC GAA      2880
Leu Arg Glu His Ile Arg Glu Glu Met Tyr Glu Arg Leu Thr Gly Glu

CAC GCG CCG TAC AAC CTC AAG TTC GTC ACC AAC GGG GTG TCC TGC ACC      2928
His Ala Pro Tyr Asn Leu Lys Phe Val Thr Asn Gly Val Ser Cys Thr

ACC GCC AGC GTG ATC GCC GCG GCG CTT AAC ATC CGT GAT CTG GAC GCC      2976
Thr Ala Ser Val Ile Ala Ala Ala Leu Asn Ile Arg Asp Leu Asp Ala

ATC GGC CCG GCC GAG GTG GAG CAG ATC CAG CGT CTG CAT ATC CTG CTG      3024
Ile Gly Pro Ala Glu Val Glu Gln Ile Gln Arg Leu His Ile Leu Leu
```

```
GTG ATG TTC AAT GCC ATG CAG CCC GGC GTG TTC GCC CTC TCC GGC TGG        3072
Val Met Phe Asn Ala Met Gln Pro Gly Val Phe Ala Leu Ser Gly Trp

GAT CTG GTC GGC GCC CTG CCG CTG GCG CCC GAG CAG GTC GAG CAC CTG        3120
Asp Leu Val Gly Ala Leu Pro Leu Ala Pro Glu Gln Val Glu His Leu

ATG GGC GAT GGC GAT ACC CGC TGG ATC AAT CGC GGC GGC TAT GAC CTC        3168
Met Gly Asp Gly Asp Thr Arg Trp Ile Asn Arg Gly Gly Tyr Asp Leu

GCC GAT CTG GCG CCG GAG GCG TCG GTC TCC GCC GAA GGC CTG CCC AAG        3216
Ala Asp Leu Ala Pro Glu Ala Ser Val Ser Ala Glu Gly Leu Pro Lys

GCC CGC TCG CTG TAC GGC AGC CTG GCC GAG CAG CTG CAG CGG CCA GGC        3264
Ala Arg Ser Leu Tyr Gly Ser Leu Ala Glu Gln Leu Gln Arg Pro Gly

TCC TTC GCC TGC CAG CTC AAG CGC ATC CTC AGC GTG CGC CAG GCC TAC        3312
Ser Phe Ala Cys Gln Leu Lys Arg Ile Leu Ser Val Arg Gln Ala Tyr

GAC ATC GCT GCC AGC AAG CAG ATC CTG ATT CCG GAT GTG CAG GCG CCG        3360
Asp Ile Ala Ala Ser Lys Gln Ile Leu Ile Pro Asp Val Gln Ala Pro

GGA CTC CTG GTG ATG GTC CAC GAG CTG CCT GCC GGC AAG GGC GTG CAG        3408
Gly Leu Leu Val Met Val His Glu Leu Pro Ala Gly Lys Gly Val Gln

CTC ACG GCA CTG AAC TTC AGC GCC GAG CCG GTC AGC GAG ACC ATC TGC        3456
Leu Thr Ala Leu Asn Phe Ser Ala Glu Pro Val Ser Glu Thr Ile Cys

CTG CCC GGC GTG GCG CCC GGC CCG GTG GTG GAC ATC ATT CAC GAG AGT        3504
Leu Pro Gly Val Ala Pro Gly Pro Val Val Asp Ile Ile His Glu Ser

GTG GAG GGC GAC CTC ACC GAC AAC TGC GAG CTG CAG ATC AAC CTC GAC        3552
Val Glu Gly Asp Leu Thr Asp Asn Cys Glu Leu Gln Ile Asn Leu Asp

CCG TAC GAG GGG CTT GCC CTG GGT GTG GTG AGC GCC GCG CCG CCG GTG        3600
Pro Tyr Glu Gly Leu Ala Leu Arg Val Val Ser Ala Ala Pro Pro Val

ATC TGA GCGC                                                           3610
Ile

CCTCTTCGCG CGCCCCGGGT CCGCCGCTAT AGTGCGCAGC GCCTGGGGCG CGCATTGCCC      3670

TCGCCGTCGA GACCAGCCCG TGTCGTTCAC TTCGCTTTTC CGCCTTGCGC TGCTGCCGCT      3730

GGCGCTGCTT GCCGCACCCG TCTGGGCGCA GACCGCCTGC CCGCCCGGCC AGCAGCCGAT      3790

CTGCCTGAGC GGCAGCTGCC TCTGCGTGGC GGCCGCCGCC AGCGATCCAC AGGCGGTCTA      3850

CGACCGCGTC CAGCGTATGG CTACGCTGGC CCTGCAGAAC TGGATCCAGC AGTCGCGCGA      3910

CCGCCTGATG GCCGGCGGCG TCGAGCCGAT ACCGCTGCAC ATCCGCTCGC AGCTCGAGCC      3970

GTATTTCGAT CTTGCCGTGC TGGAGAGTGC GCGGTACCGC GTCGGCGACG AGGTGGTGCT      4030

GACTGCCGGC AACACCCTGC TGCGCAACCC GGACGTCAAT GCCGTGACCC TGATCGACGT      4090

CATCGTCTTC CGCCACGAGG AGGATGCCCG GGACAACGTC GCGCTCTGGG CCCATGAGCT      4150

CAAGCACGTC GAGCAATATC TGGACTGGGG CGTCGCCGAG TTCGCCCGGC GCTATACGCA      4210

GGATTTCCGT GCCGTGGAGC GCCCGGCCTA TGCGCTGGAG CGTGAGGTGG AAGAGGCCCT      4270

GCGCGAGACG CAGACGCGGC GCTGAGCCAG CTGATCGGTG CTGCTGCCCG CACTGGGCTG      4330

AAGCCCACCA ATGACGCCGG CGAAAACGAA AAACCCCGCC GAGGCGGGGT TTCTGACGCG      4390

GGTTGTGCGG TCAGCTCAGA ACGCCGGGAC CACGGCGCCC TTGTACTTTT CCTCGATGAA      4450

CTGGCGTACT TGCTCGCTGT GCAGCGCGGC AGCCAGTTTC TGCATGGCAT CGCTGTCCTT      4510

GTTGTCCGGA CGGGCGACCA GAATGTTCAC GTATGGCGAG TCGCTGCCCT CGATCACCAG      4570

GGCGTCCTGG GTCGGGTTCA GCTTGGCTTC CAGCGCGTAG TTGGTGTTGA TCAGCGCCAG      4630

GTCGACCTGG GTCAGCACGC GCGGCAGAGT CGCGGCTTCC AGTTCGCGGA TCTTGATCTT      4690

CTTCGGGTTC TCGGCGATGT CTTCGGCGTG GCGGTGATGC CGGCGCCGTC CTTCAGACCG      4750

ATC                                                                    4753
```

The present invention also provides a recombinant plasmid containing the trehalose synthase gene with the above nucleotide sequence. In a preferred embodiment, the present invention provides are combinant plasmid pCJ104 in which the 4.7 kb Sau3AI DNA fragment of the trehalose synthase gene of the present invention is cloned into vector plasinid pUC18. This allow for the efficient and high expression of the trehalose synthase gene. In a more preferred embodiment, the present invention provides a recombinant plasmid pCJ122 in which the 2.5 kb BamHI-BglII DNA fragment of the trehalose synthase gene of the present invention is included in a vector plasmid pUC18. allowing for a higher expression of the trehalose synthase gene.

The present invention provides a transformed E. coli with a recombinant plasmid containing the trehalose synthase gene with the above nucleotide sequence. In a preferred embodiment, the present invention provides a transformed E. coli with a recombinant plasmid pCJ104, allowing for production of high levels of the trehalose synthase protein. In a more preferable embodiment, the present invention provides a transformed E. coli with the recombinant plasmid pCJ122, allowing for production of even higher levels of the trehalose synthase protein.

The present invention provides a process for producing trehalose which comprises reacting the trehalose synthase protein with the above amino acid sequence with maltose solution to obtain trehalose.

The present invention provides a process for producing trehalose which comprises crushing a transformed E. coli with a recombinant plasmid containing the trehalose synthase gene with the above nucleotide sequence and reacting the crushed cells with maltose solution to obtain trehalose. In a preferred embodiment, the present invention provides a process for producing trehalose which comprises crushing a transformed E. coli with plasmid pCJ104, centrifuging the crushed cells and reacting the resulting supernatant with maltose solution to obtain trehalose. In a more preferable embodiment, the present invention provides a process for producing trehalose which comprises crushing a transformed E. coli with plasmid pCJ122, centrifuging the crushed cells and reacting the resulting supernatant with maltose solution to obtain trehalose.

DETAILED DESCRIPTION OF THE INVENTION

Figure 1:
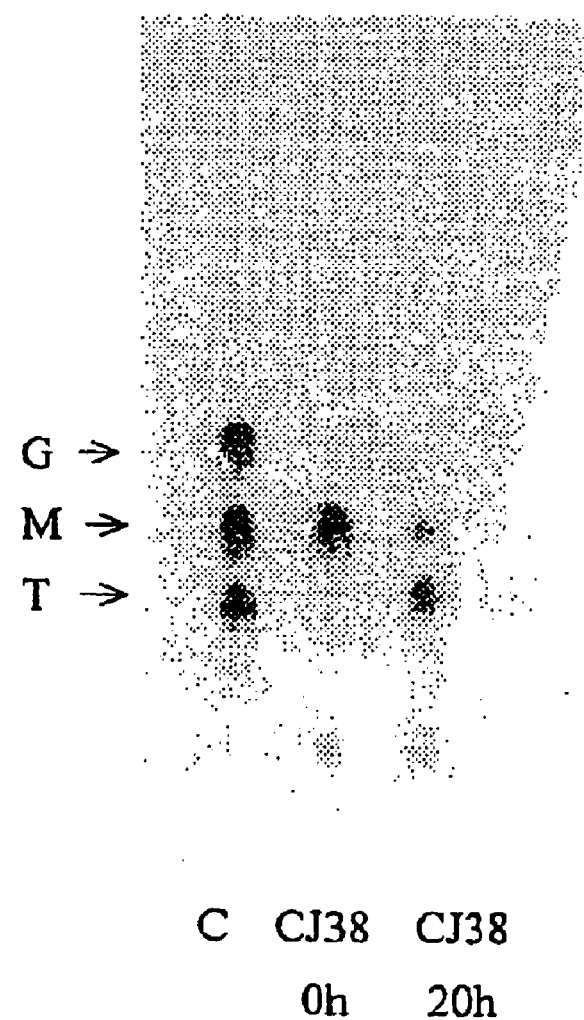
FIG. 1 shows an analysis of saccharides by thin-layer chromatography to which a reaction solution containing sonicated liquid from Pseudomonas stutzeri CJ38 and maltose solution was subjected. The symbols G, M and T indicate glucose, maltose and trehalose, respectively. In the first lane of the gel shown in FIG. 1 is a control containing glucose, maltose and trehalose.

A microorganism which produces trehalose from maltose by trehalose synthase was isolated from soil and identified as having the morphological and physiological characteristics of Pseudomonas stutzeri. Pseudomonas stutzeri has not been reported to convert maltose into trehalose. Therefore, the microorganism isolated by us can be recognized as a novel Pseudomonas stutzeri strain and has been designated as Pseudomonas stutzeri CJ38.

We constructed the restriction map of a recombinant plasmid pCJ104 of the present invention using various restriction enzymes. Two trehalose synthase gene sequences are known (Biochim. Biophys. Acta 1996, 1290, 1–3 and Biochim. Bophys. Acta 1997, 1334, 28–32). The comparison of the present and known restriction maps revealed that pCJ104 represents different patterns from those known.

Trehalose synthase proteins from known microorganisms have shown similarities in their N-terminus. However, it was found that the N-terminal sequence of the trehalose synthase protein of the present invention is not identical with those of known trehalose synthase proteins. The results are shown in Table 1 below.

TABLE 1

N-terminal Sequences of Trehalose Synthase Proteins

| Source of Trehalose Synthase | | N-terminal Sequence |
|---|---|---|
| Known Microbes | Thermus aquaticus ATCC 33923 | M-D-P-L-W-Y-K-D-A-V-I-Y-Q- (SEQ ID NO: 3) |
| | Pimelobacter sp. R48 | S-T-V-L-G-E-E-P-E-W- F-R-T-A-V-F-Y-E- (SEQ ID NO: 4) |
| | Pseudomonas putida H262 | G-K-W-P-R-P-A-A-F-I-D- (SEQ ID NO: 5) |
| Transformed E. coli of the Present Invention | | S-I-P-D-N-T-Y-I-E-W-L-V- (SEQ ID NO: 6) |

The nucleotide sequence of 4.7 kb Sau3AI fragment within a recombinant plasmid pCJ104 of the present invention and the amino acid sequence of a trehalose synthase protein expressed therefrom were determined (SEQ ID NO: 1).

In addition, the intact sequence of a trehalose synthase protein of the present invention was compared to those of the trehalose synthase proteins disclosed in Biochim. Biophys. Acta 1996, 1290, 1–3 and Biochim. Biophys. Acta 1997, 1334, 28–32. The comparison revealed that there are no similarities between them.

The enzymatic conversion reaction was carried out using crushed E. coli transformant including recombinant plasmids pCJ104 or pCJ122. As a result, the titer of trehalose synthase enzyme from the crushed cells of the present invention was considerably higher than that from the wild type Pseudomonas stutzeri CJ38.

The properties and availabilities of the plasmids and microorganisms used in and prepared by the present invention are shown in Table 2 below.

TABLE 2

| Microbes and Plasmids | Properties | Availability |
|---|---|---|
| Pseudomonas stutzeri CJ38 | Wild type strain producing the trehalose synthase enzyme of the present invention | KFCC-10985 |
| E. coli NM522 | hsdΔ5, Δ(lac pro) [F', Pro+, lacI^qZΔM15] | Amersham |
| E. coli ATCC 35467 | [malP,Q::Tn5 ompBCS1 F− araD139Δ(argF− lac) 205U169 rpsL150 relA1 flbB5301 deoC1 ptsF25] | ATCC |
| pCJ104 | pUC18 containing 4.7 kb Sau3AI DNA fragment (trehalose synthase gene), Ap^r | Constructed |
| pCJ121 | pUC18 containing 3.35 kb KpnI DNA fragment (trehalose synthase gene), Ap^r | Constructed (Control) |
| pCJ122 | pUC18 containing 2.5 kb BamHI-BglII DNA fragment (trehalose synthase gene), Ap^r | Constructed |
| pCJ123 | pUC18 containing 1.2 kb BamHI-EcoRI DNA fragment | Constructed (Control) |
| pUC18 and pUC19 | Ap^r, 2.7 kb | New England Biolabs |

Nutrient medium (0.3% broth, 0.5% peptone, pH 6.8) and LB medium (1% tryptone, 0.5% yeast extract, 1% NaCl, pH 7.0) were used for cultivation of Pseudomonas stutzeri and E. coli, respectively. For the culture of cells transformed by electroporation, SOC medium (2% tryptone, 0.5% yeast extract, 10 mM NaCl, 2.5 mM KCl 10 mM $MgCl_2$, 10 mM $MgSO_4$, 20 mM glucose) was used. MacConkey agar medium (4% bacto MacConkey agar base, 2.0% maltose, pH 7.0) was used in cloning the trehalose synthase gene. Ampicillin was added in a concentration of 50 mg/L. Gene Pulser (Bio-Rad) was used in transformation of E. coli by electroporatior. The genetic manipulation used in the present invention was carried out in accordance with procedures described in Molecular Cloning, Laboratory Manual, 2$^{nd}$ ed., Sambrook, J., E. F. Frishc and T. Maniatis and Guide to Molecular Cloning Techniques, Methods in Enzymol. Vol. 152, Berger, S. L., A. R. Kimme.

The enzymatic reaction is conducted at pH 6.0 to 11, preferably pH 7.0 to 10, and at temperatures of 4° C. to 45° C., preferably 20° C. to 40° C. Maltose can be used as a substrate in a concentration of less than 50%. The trehalose synthase enzyme can be used in a pure form or in crushed cells.

The following examples illustrate the present invention. From the foregoing description and the following examples, it is believed that those skilled in the art would be able to carry out the invention completely.

EXAMPLE 1

Screening of Microorganism

A platinum loop of microorganisms, isolated from soil, was inoculated in a 500 ml Erleuneyer flask containing 50 ml of LB culture solution (0.5% of yeast extract, 1.0% of bactotrypton, 0.5% of salt) and cultured at 28° C. for 2 days. The culture was centrifuged at 4° C., 8,000 rpm, for 5 minutes. The cells were collected and washed with physiological saline. The washed cells were suspended in 10 ml of phosphate buffer solution (10 mM, pH 7.0). The cells were crushed by an ultrasonicater and the crushed cells were centrifuged at 4° C., 1.200 rpm. for 20 minutes and the supematant was used as a crude enzymatic solution. The concentration of the protein in the crude enzymatic solution was determined by the Bredford method. 100 μg of protein was mixed with 20 μl of 100 mM maltose and 10 μl of 100 mM phosphate buffer solution (pH 7.0). Distilled water was added to the mixture until the total volume reached 100 μl and the reaction occurred at 30° C. for 20 hours. The saccharides present in the reaction solution were analyzed by TLC, HPLC, and GC.

EXAMPLE 2

Analysis of Trehalose by Thin-layer Chromatography (FIG. 1)

After the reaction was completed, 5 μl of the reaction solution were spotted on Kieselgel 60 TLC (Merck, Germany) and placed in a vessel containing a solvent system of n-butanol-pyridine-water (7:3:1) to develop the specimens. It was sprayed with a solution of 20% sulfuric acid in methyl alcohol and dried at 100° C. for 10 minutes. The saccharides in the specimens were thus specified. Among at least 1,000 soil microorganisms investigated, two were confirmed to have the ability to convert maltose into trehalose. FIG. 1 shows that trehalose did not exist in the specimens prior to the reaction but, after completion of the reaction, saccharides were detected at the site of a standard trehalose specimen.

EXAMPLE 3

Figure 2:
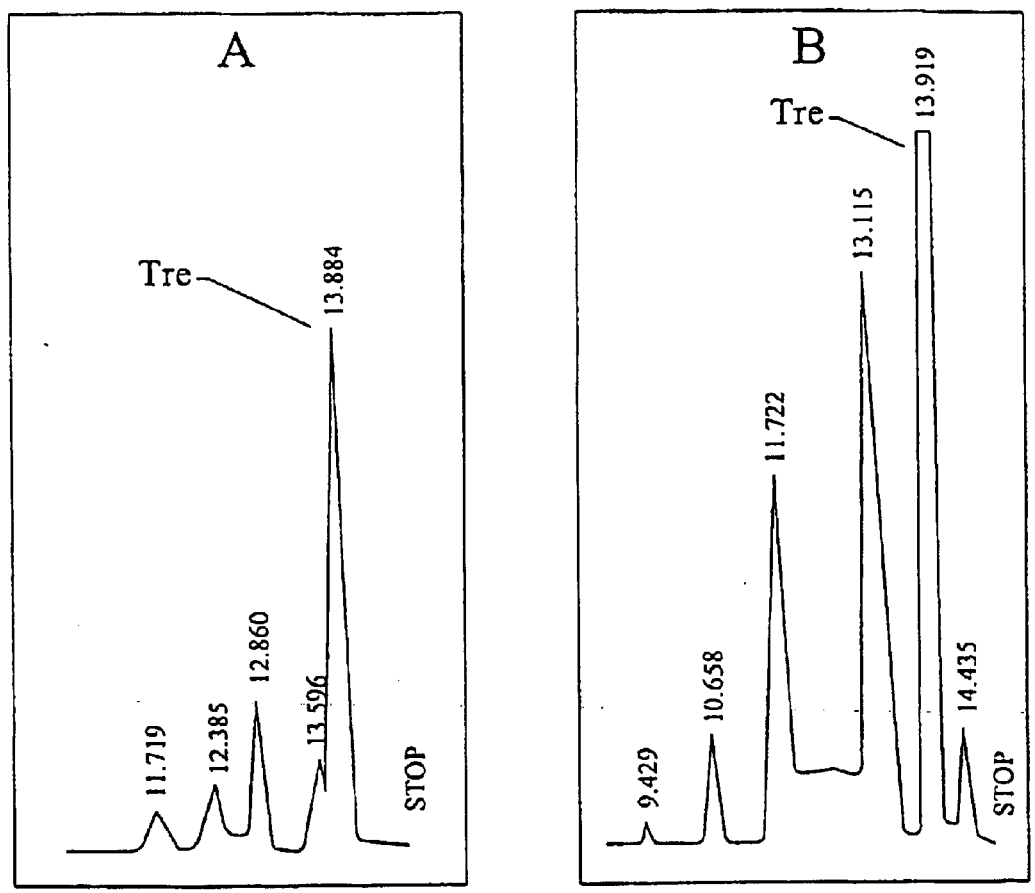
FIG. 2 shows an analysis of saccharides by gas chromatography to which a reaction solution (A) containing sonicated liquid from Pseudomonasstutzeri CJ38 and maltose solution and a standard trehalose specimen (B) were subjected. The symbol Tre indicate trehalose.

Analysis of Trehalose by Gas Chromatography (FIG. 2)

After completion of the reaction, 10 μl of the reaction solution was dried by a reduced pressure dryer. The dried product was dissolved in 20 μl of dimethylformamide and the resulting solution was mixed with the same volume of bis(trimethyl)trifluoracetamide to form trimethylsilane derivatives. One μl of aliquot was used in GC analysis. As shown in FIG. 2, the peak of the reaction solution was observed to occur at the same time as with a standard trehalose specimen.

EXAMPLE 4

Figure 3:
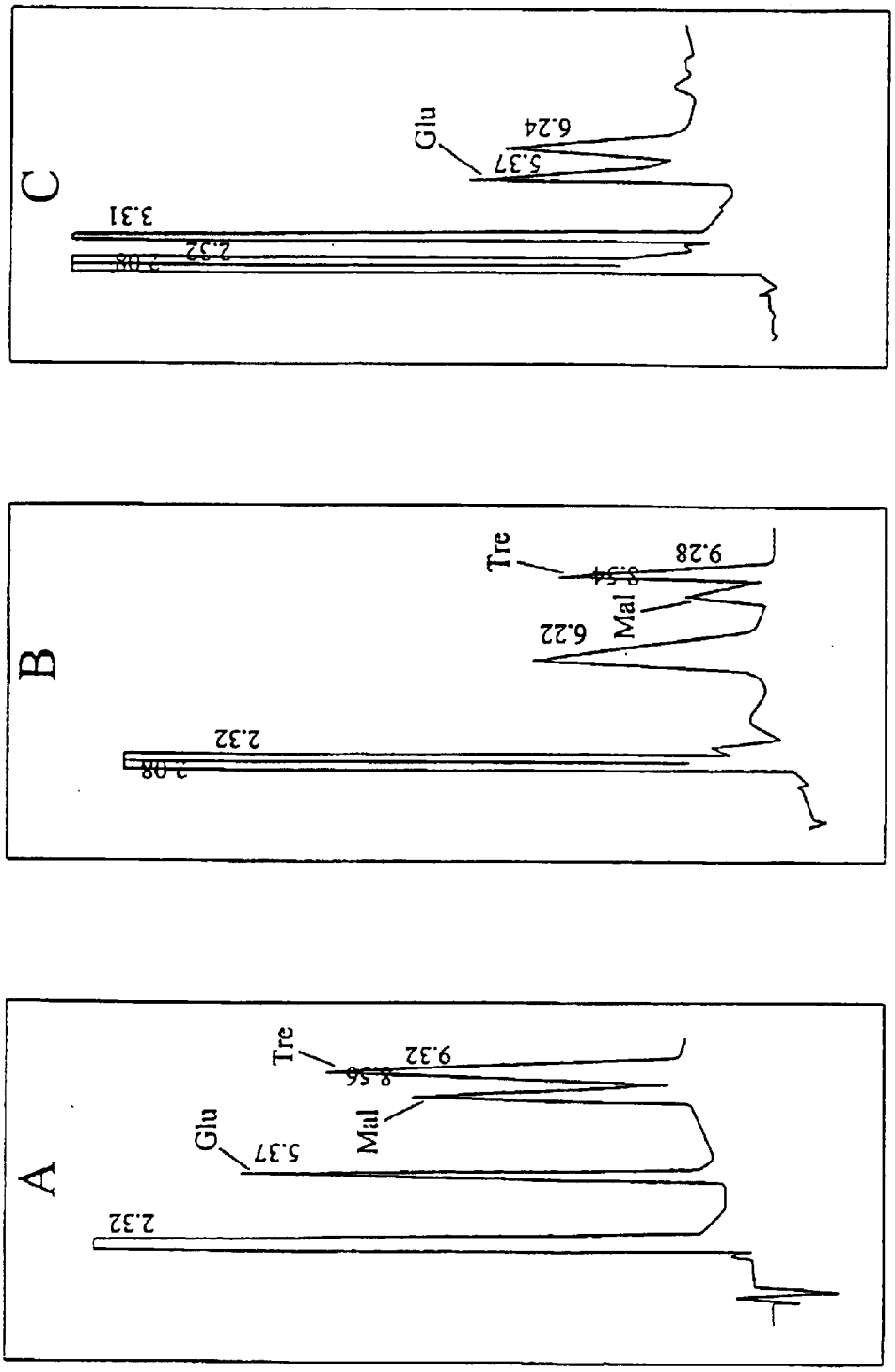
FIG. 3 shows an analysis of saccharides by high performance liquid chromatography to which a standard trehalose specimen (A), and specimens (B) and (C) were subjected. Specimen (B) was obtained just after a solution containing sonicated liquid from Pseudomonas stutzeri CJ38 and maltose solution was reacted completely. Specimen (C) was obtained by adding irehalase to a reaction solution containing sonicated liquid from Pseudomonas stutzeri CJ38 and maltose solution after completion of their reaction. The symbols Tre, Mal and Glu indicate trehalose, maltose and glucose, respectively.

Analysis of Trehalose by High Performance Liquid Chromatograpby (FIG. 3)

After the reaction was completed, half of the reaction solution was mixed with the same volume of phenol to remove proteins. The specimen solution thus obtained was used in the HPLC analysis. The peak of the specimen was observed to occur at the same time as with a standard trehalose specimen. The remaining half of the reaction solution was heated to 100° C. for 10 minutes to terminate enzyme activity. It was reacted at 37° C. for 10 minutes with trehalase (Sigma) which specifically acts on α-1,1-trehalose. After completion of the reaction, the solution was mixed with the same volume of phenol solution to remove proteins. The solution obtained thus was subjected to HPLC, and as a result the peak disappeared at the same time as with a standard trehalose.

EXAMPLE 5

Identification of Microorganism Capable of Converting Maltose into Trehalose

The soil microorganism of the present invention was observed by electron microscope and is characterized by rod shaped bacteria with flagellum. It was also characterized as aerobic by an O/F test and by Gram-negative. The physiological characteristics of the microorganism are summarized in Table 1. These characteristics of the present microorganism were compared to those of microorganisms described in *Bergy's Manual of Systemic Bacteriology*, 1984 and in patent publications, and it was classified as *Pseudomonas stutzeri*, because it is almost identical to that microorganism, physiologically and morphologically.

TABLE 1

| DP3 – | OFG + | GC + | ACE – | ESC – | PLI – |
|---|---|---|---|---|---|
| URE – | CIT + | MAL + | TDA – | PXB – | LAC – |
| MLT + | MAN + | XYL – | RAF – | SOR – | SUC – |
| INO – | ADO – | COU – | H2S – | ONP – | RHA – |
| ARA – | GLU – | ARG – | LYS – | ORN – | OXI – |
| TLA – | | | | | |

EXAMPLE 6

Figure 4:
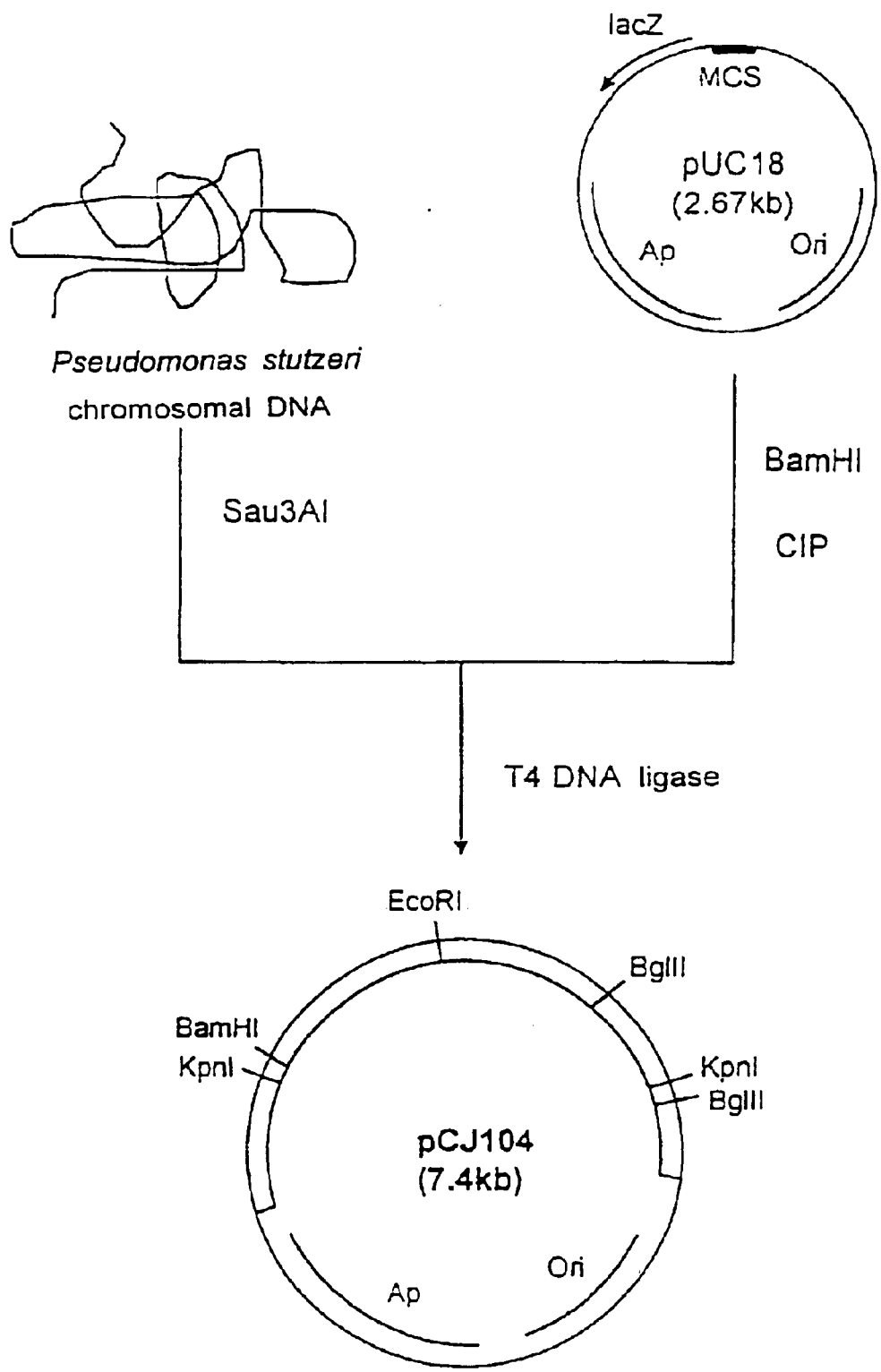
FIG. 4 shows a construction map of a recombinant plasmid pCJ104 including a trehalose synthase gene of the present invention.

Cloning of Trehalose Synthase Gene (FIG. 4)

(1) Isolation of Chromosomal DNA from *Pseudomonas stutzeri*

Pseudomonas siutzeri was grown in a nutrient medium and at an early resting stage, cells were recovered by centrifugation. The recovered cells were washed twice with TE solution (10 mM Tris-HCl, pH 8.0, 1 mM EDTA, pH 8.0). The washed cells were suspended in 20 mL of STE buffer (20% sucrose, 10 mM Tris, pH 8.0, I mM EDTA, pH 8.0) and 5 mg/mL of lysozyme and RNase A were added to the suspension. The reaction occurred at 37° C. for 2 hours. After the reaction was completed, SDS was added up to a concentration of 1% and the reaction continued at 37° C. for 30 minutes. This solution was reacted with the same volume of phenol for 4 hours and was subjected to centrifugation. SM NaCl was added to the resulting supernatant until its concentration reached 0.1 M. Using a glass bar, a two-fold volume of anhydrous ethanol was added to obtain chromosomal DNA. The chromosomal DNA was washed with 70% ethanol and dissolved in TE solution for use in the next experiment.

(2) Preparation of Genomic Library

Figure 5:
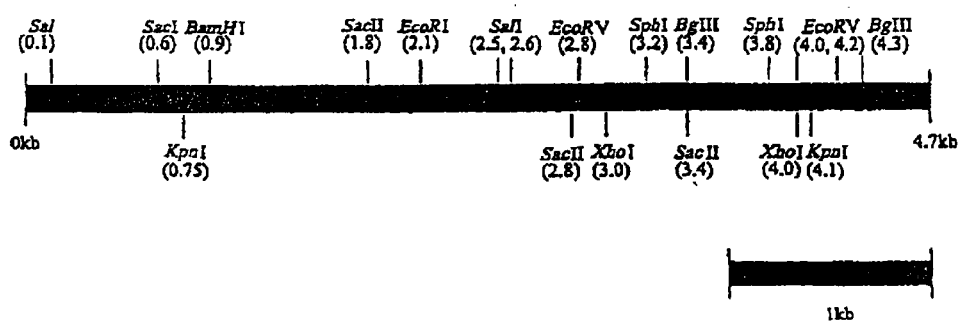
FIG. 5 shows a restriction map of a 4.7 kb Sau3AI fragment within a recombinant plasmid pCJ104 of the present invention.

The pure chromosomal DNAs isolated from *Pseudomonas stutzeri* were partially digested with restriction enzyme Sau3AI at 37° C. for 15 to 30 minutes. The restriction enzyme was inactivated with heat and agarose gel electrophoresis was carried out to obtain 3 to 10 kb DNA fragments. As shown in FIG. 5, plasmid pUC18 was digested with BamHI and was treated with calf intestinal phosphatase. The cleaved DNAs were mixed with 3 to 10 kb DNA fragments previously obtained and ligation with T4 DNA ligase was allowed at 15° C. for 16 hours. The recombinants thus obtained were used for tranformation. The transformation was carried out by electroporation as follows. *E. coli* NM522 was cultured on LB medium for 14 to 15 hours. The resulting culture. was inoculated on 1L LB so that initial absorbency became 0.07 to 0.1 at 600 nm, and then cultivation was allowed until the absorbency reached 0.8. The cells were centrifuged and suspended in 1L of HEPES [N-(2-hydroxyethyl)piperazine-N-(2-ethanesulfonic acid)] buffer solution. The cells were again centrifuge suspended in 500 ml of cold sterile deionized distilled water. The cells were again centrifuged and suspended in 20 ml of 10% glycerol solution. The cells were again centrifuged and suspended in 2 to 3 ml of 10% glycerol solution so that the cell concentration was adjusted to $2$–$4\times10^{10}$/ml. The cell suspension was rapidly frozen and stored at 70° C. The frozen cells could be used for about one month during which time their transformation frequency did not decrease. 40 µL of frozen cell suspension was thawed in ice and the restored suspension was mixed with the ligated DNA solution. The mixture was put in a gene pulser cuvette with a diameter of 0.2 cm and the capacitance and strength of electric field was fixed at 25 uF and 12.5 kV/cm, respectively. After a single electric pulse was passed at resistance of 200 to 400 Ω, 1 ml of SOC medium was immediately added and cultured at 37° C. for 1 hour. The culture was streaked on LB-ampicillin agar medium and cultivation was allowed for 24 hours to obtain at least fifty thousand colonies. These colonies were together cultured in LB broth for 2 hours. DNA was purely isolated using an alkaline lysis and the genomic library was constructed therefrom.

(3) Cloning of Trehalose Synthase Gene *E. coli* ATCC35467, which is unable to utilize maltose as a carbon source, was transformed with the genomic library obtained from the above by electroporation. The transformed cells were streaked on a MacConkey-ampicillin agar medium containing 20 g/L of maltose. Once the trehalose synthase gene of Pseudomonas stutzeri is introduced into *E. coli*, maltose is converted into glucose by the trehalase present in *E. coli*. As the resulting glucose is metabolized, pH decreases and thereby the color of the colonies on the MacConkey agar medium changes from yellowish to red. This principle was applied to the present cloning system. The transformed *E. coli* ATCC35467 with the genomic library was cultured on a MacConkey agar medium to obtain red colonies. The isolation of plasmid DNA revealed that it contained about 4.7 kb DNA fragient. The plasmid was designated as pCJ104. To assay enzymes, *E. coli* ATCC35467/pUC18 (control), *E. coli* ATCC35467/pCJ104 and wild type *Pseudomonas stutzeri* CJ38 were cultured. *E. coil* cells were grown on a LB medium until their early resting stage. *Pseudomonas stutzeri* CJ38 was grown on a nutrient medium. The cells were separated by centrifugation and crushed. The crushed cells were reacted with 20% maltose as substrate in 20 mM diethanolamine as buffer solution at pH of 8.5 to 9.0 and a temperature of 35° C. 1.0% trichloroacetic acid was added to the reaction solution, which was then subjected to centrifuigation and high performance liquid chromatography to assay the quantities of maltose and trehalose. The results are shown in Table 3 below.

TABLE 3

| | Enzyme Titration | |
|---|---|---|
| Microorganisms | Specific activity of enzyme (U*/mg of protein) | Culture Titer (U/ml of culture solution) |
| *Pseudomonas stutzeri* CJ38 | 0.1 | 0.023 |
| *E. coli* ATCC35467/pUC18 | 0 | 0 |
| *E. coli* ATCC35467/pCJ104 | 0.26 | 0.175 |

*U-µmol trehalose/minutes--

Example 7

Restriction Map Construction of Trehalose Synthase Gene (FIG. 5)

The plasmid pCJ104 was separated using conventional methods and treated with various restriction enzymes to construct a restriction map.

The plasmid pCJ104 was subjected to single, double, and triple-digest procedures using about twenty restriction enzymes, such as AatII, BamHI, BglIII, SmaI, EcoRI, EcoRV, KpnI, NcoI, NdeI, PstI, SacI, SacII, SalI, SphI and XhoI. DNA fragments were analyzed by electrophoresis through agarose gel and compared to construct the restriction map.

EXAMPLE 8

Figure 6:
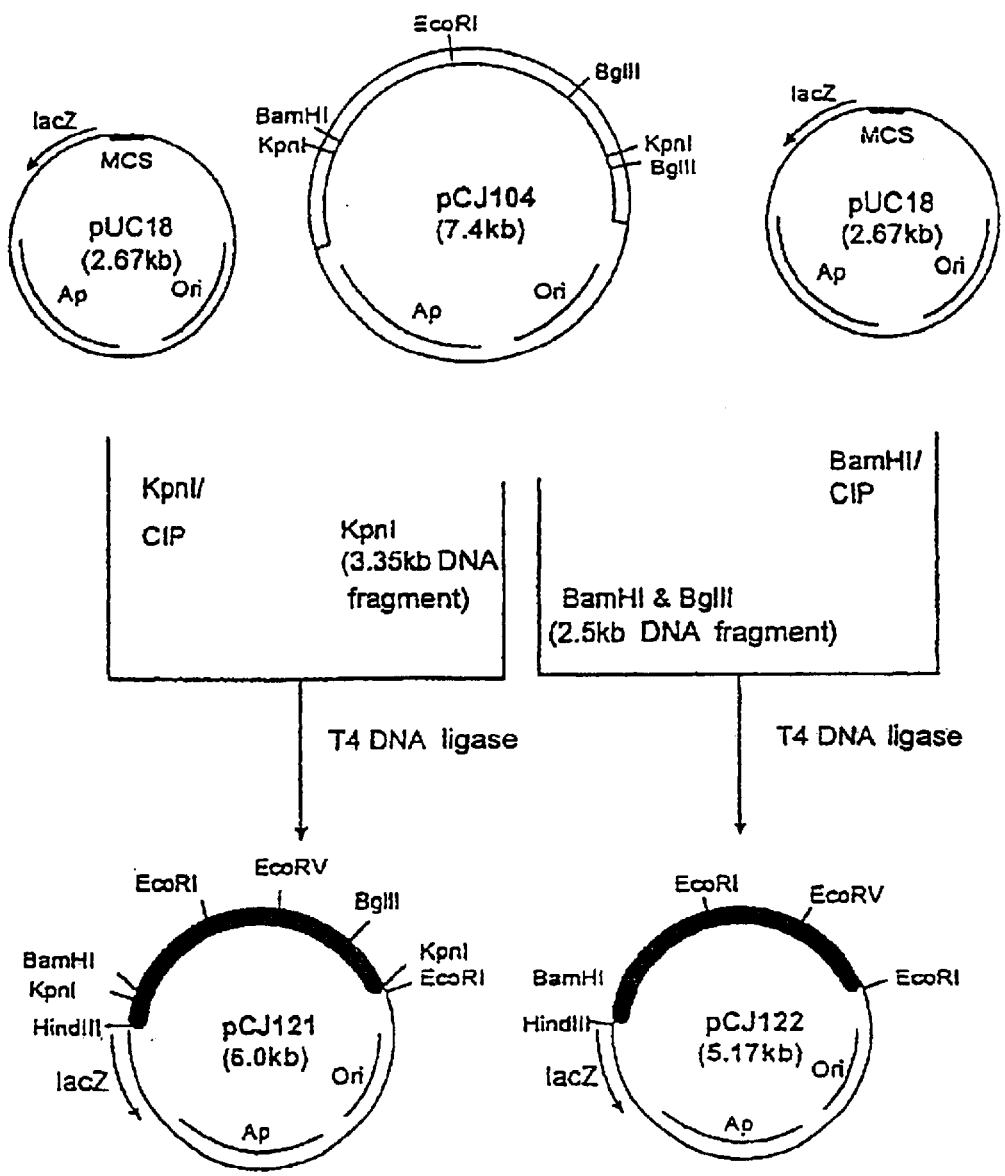
FIG. 6 shows a construction map of recombinant plasmids pCJ121 and pCJ122 of the present invention.

Subcloning of Trehalose Synthase Gene and Enzyme Assay (1) Subcloning of Trehalose Synthase Gene (FIG. 6)

A subcloning was carried out to determine the sites of the trehalose synthase gene in 4.7 kb plasmid pCJ104. The plasmid pCJ104 was cleaved with KpnI and a 3q35 kb fragment was isolated. This fragment was introduced into vector pUCI 18/KpnI/CIP and *E. coli* NM522 was transformed with the resulting recombinant. The recombinant plasmid pCJ121 with a directional cloning of 3.35 kb fragment into pUC18/KpnI was constructed. In addition, the plasmid pCJ104 was cleaved with double digestions of BamHI and BglII. The 2.5 kb BamHI-BglII fragment thus obtained was purified and ligated into pUC18/BamHI/CIP, followed by transformation of *E. coli* NM522 with the recombinant. The recombinant plasmid pCJ122 with directional cloning of 2.5 kb BamHI-BglII fragment into pUC18/BamHI was constructed. Finally, the plasmid pCJ104 was double-digested with BamHI and EcoRI and the resulting 1.2 kb BamHI-EcoRI fragment was purified. This fragment was ligated into vector pUCI18/BamHI/EcoRI and *E. coli* NM522 was transformed with the recombinant. The recombinant plasmid pCJ123 was constructed.

*E. coli* ATCC35467 was transformed with each of the constructed recombinant plasmids. The transformant were cultured on a MacConkey-ampicilline agar medium containing 2.0% maltose (20 g/L) and the color of the colonies formed therefrom was observed. It was observed that the *E. coli* ATCC35467 carrying pCJ121 and pCJ122 formed red colonies but that the *E. coli* ATCC35467 carrying pCJ123 formed yellow colonies since it did not decompose maltose. Therefore, it can be seen that the trehalose synthase gene is located in the larger 2.5 kb BamHI-BglII fragment, rather than in the 1.2 kb BamHI-EcoRI fragment.

(2) Titration of Trehalose Synthase of Transformant Containing Subcloned Plasmid Transformed *E. coli* ATCC35467/pCJ121, ATCC35467/pCJ122 and ATCC35467/pCJ123 were cultured on an LB-Ap medium until the early resting stage. The cells were recovered by centrifuigation and washed twice with an appropriate volume of 20 mM diethanolamine solution. The washed cells were suspended in an appropriate volume of 20 mM diethanolamine solution and crushed by ultrasonicater. The crushed cells were centrifuged and the supematant obtained therefrom was used as enzymatic liquid. The supematant was reacted with 20% maltose solution containing 20 mM diethanolamine, pH 8.5 to 9.0 at 35° C. 1.0% trichloroacetic acid was added to the reaction solution, and centrifugation and HPLC were conducted for analysis. One unit of enzyme activity was defined as a quantity of enzyme when it produced 1 $\mu$l of trehalose per minute. The results are shown in Table 5 below.

According to the double titration, the enzyme titer of *E. coli* ATCC35467/pCJ122 was the highest *E. coil* ATCC35467/pCJ122 was cultured in high density under the conditions described in Table 6 below in 5 L fermenter. As a result, the non-enzymatic activity was 5.0 U/mg of protein, equal to that obtained by culturing it on an LB medium and the titer of the trehalose synthase enzyme in the high density culture was increased to 30 U/ml of culture (Table 5). The non-enzymatic activity and culture titer of *E. coli* ATCC35467/pCJ122 were increased 50 times and about 1,300 times, respectively, compared to wild type *Pseudomonas stutzeri*.

TABLE 5

| Microorganisms | Specific activity of enzyme (U/mg of protein) | Culture Titer of 5 L Fermenter (U/ml of culture) |
| --- | --- | --- |
| E. coli ATCC35467/pCJ121 | 0.43 | — |
| E. coli ATCC35467/pCJ122 | 4.95 | 30 |
| E. coli ATCC35467/pCJ123 | 0 | — |

TABLE 6

| Fermentation Medium | g/L | Culture Condition |
| --- | --- | --- |
| glycerol | 50 | pH 7.0 |
| $(NH_4)_2SO_4$ | 6 | Temperature of 33° C. |
| $KH_2PO_4$ | 2 | 800 rpm |
| $MgSO_4 \cdot 7H_2O$ | 1 | 1.0 vvm |
| Yeast Extract | 5 | |
| Trace Elements | 1 ml | |
| Amino Acids (Threonine, Leucine, Isoleucine, Valine, Histidine, Arginine) | 0.5 | |

What is claimed is:

1. An isolated trehalose synthase protein comprising the amino acid sequence as recited in SEQ ID NO: 2.

2. An isolated trehalose synthase gene comprising the nucleotide sequence as recited in SEQ ID NO: 1.

3. A recombinant plasmid containing the trehalose synthase gene of claim 1.

4. The recombinant plasmid according to claim 1 which is recombinant plasmid pCJ122.

5. A transformed *E. coli* with the recombinant plasmid of claim 1.

6. The transformed *E. coli* according to claim 5 in which the recombinant plasmid is pCJ122.

7. A process for producing trehalose which he trehalose synthase enzyme of claim 1 with obtain trehalose.

8. A process for producing trehalose which comprises lysing the transformed *E. coli* of claim 5, centrifurgin lysed bacteria, and reacting the resulting supernatant with maltose solution to obtain trehalose.

9. An isolated microorganism *Pseudomonas stutzeri* CJ38 produces trehalose from maltose.

* * * * *